United States Patent [19]

Fraim

[11] 4,070,155
[45] Jan. 24, 1978

[54] APPARATUS FOR CHROMATOGRAPHICALLY ANALYZING A LIQUID SAMPLE

[75] Inventor: Freeman W. Fraim, Lexington, Mass.

[73] Assignee: Thermo Electron Corporation, Waltham, Mass.

[21] Appl. No.: 760,605

[22] Filed: Jan. 19, 1977

[51] Int. Cl.² .............................................. G01N 31/08
[52] U.S. Cl. ........................... 23/230 PC; 23/253 PC; 23/254 R; 73/61.1 C
[58] Field of Search ........ 23/230 PC, 253 PC, 232 R, 23/254 R, 254 E, 255; 73/23.1, 61.1 C; 55/67, 386; 210/24 C, 31 C

[56] References Cited
U.S. PATENT DOCUMENTS

| | | | |
|---|---|---|---|
| 3,835,322 | 9/1974 | Komatsu | 23/254 R |
| 3,877,875 | 4/1975 | Jones et al. | 23/230 PC |
| 3,973,910 | 8/1976 | Fine | 23/253 PC |
| 3,996,002 | 12/1976 | Fine | 23/253 PC |
| 3,996,003 | 12/1976 | Fine et al. | 23/253 PC |
| 3,996,004 | 12/1976 | Fine et al. | 23/253 PC |
| 3,996,008 | 12/1976 | Fine et al. | 23/253 PC |
| 3,996,009 | 12/1976 | Fine et al. | 23/253 PC |

Primary Examiner—R.E. Serwin
Attorney, Agent, or Firm—James L. Neal; David W. Gomes

[57] ABSTRACT

A chromatographic system is provided for detecting in a liquid sample the presence of organic nitrogen containing compounds. A liquid chromatograph separates constituents of the liquid sample and discharges the separated constituents in a timewise distribution. Effluent from the chromatograph is atomized into a converter and there oxidized at a temperature approximately in the range 600° to 800° C for converting the nitrogen in the organic nitrogen containing compound to nitric oxide. Sufficient oxygen is supplied to the converter to fully oxidize the sample introduced therein. Effluent is transferred from the converter to a nitric oxide detector which measures the nitric oxide present in the converted sample and thereby provides a measurement of the organic nitrogen containing compound in the sample.

In an alternate embodiment for use with sulphur containing organic compounds, the effluent from the chromatograph, when atomized into the converter and oxidized, may be transferred to a sulphur dioxide detector. The indication of sulphur dioxide present in the sulphur dioxide detector corresponds to the content of organic sulphur containing compounds in the sample.

14 Claims, 8 Drawing Figures

APPARATUS FOR CHROMATOGRAPHICALLY ANALYZING A LIQUID SAMPLE

BACKGROUND OF THE INVENTION

Chromatography is an analytical science in which a complex mixture is separated into its individual constituents as the constituents can be identified and quantified. Since its advent in the nineteen sixties, gas chromatography has caused a major revolution in organic chemistry. More recently, there has been developed apparatus for high pressure liquid chromatography in which a liquid sample is introduced into a chromatographic column and then, instead of being vaporized, is kept in the liquid phase during the separation process. Liquid chromatography offers numerous advantages over gas chromatography. Among them, a liquid chromatographic column can be operated at ambient temperature. Also, separation of the components of the sample mixture in the liquid phase facilitates a degree of control not easily available with gas chromatograph columns. Some compounds which tend to be broken down or suffer unwanted molecular reorganization in a gas chromatographic column can be separated quite readily in a liquid chromatographic column. For example, many organic compounds, because of their polarity, high molecular weight or thermal instability, are not amenable to gas chromatographic techniques but are well suited to high pressure liquid chromatographic analysis. On the other hand, state of the art detectors interface quite readily with gas chromatographs but liquid chromatography tends to be limited by poor sensitivity of the compatible detectors. Substantial effort has been devoted to improvement of the most widely used detectors; refractive index and ultra absorbance. Other techniques have been explored including micro absorption, polarographic, and conductivity detectors.

The early Nobel prize winning work of A. J. P. Martin and R. L. M. Synge *Biochem. J.* 35, 81, 1358 (1941) set forth the basic liquid chromatographic techniques used in systems today. However, practical application for these techniques have been severely limited by available detectors. As a result, liquid chromatographic analysis is generally a lengthy procedure, often taking hours and even days. The availability of high pressure pumps (in excess of 5,000 psi) permits the use of long, narrow bore (e.g. 1 mm) columns having small diameter packing particles. Use of such small diameter columns minimizes the time required for liquid chromatographic analysis but the level of sensitivity is still below that associated with gas chromatographic systems.

SUMMARY OF THE INVENTION

It is an object of the present invention to provide a method and apparatus for high speed liquid chromatographic analysis of a sample.

It is another object of this invention to provide a method and apparatus for high sensitivity liquid chromatographic analysis of a sample in a liquid phase solvent.

It is also an object of this invention to provide a high speed, high sensitivity liquid chromatographic methods and apparatus for detecting the presence of nitrogen containing organic compounds in a sample in a liquid phase solvent.

It is a further object of this invention to provide a high sensitivity, high speed liquid chromatographic method and apparatus for detecting the presence of sulphur in sulphur containing organic compounds in a liquid phase solvent.

The invention involves a liquid chromatograph associated with an oxidizing conversion means and an atomizing nozzle for introducing effluent from the chromatograph into the conversion means. Discharge from the conversion means is processed by a gas detector to yield information about the chromatographic effluent.

According to a preferred embodiment of the invention, a sample in a liquid phase solvent is passed through a high pressure liquid chromatograph to separate the constituents in a timewise fashion. Typically, the high pressure liquid chromatograph includes a high pressure pump, a sample injector, a chromatographic column and an output port from the chromatograph column. The effluent from the chromatographic column is received by an atomizing nozzle for introduction into an oxidizing sample converter. The nozzle receives the chromatographic effluent along one path and, along another path, a supply of oxygen which is sufficient to fully oxide the effluent from the chromatograph. An excess of oxygen is preferred to assure that complete oxidation will occur in the converter. Optionally, an inert gas may be supplied with the oxygen, either in mixture with it or along a separate path, to assist in optimizing the temperature profile within and along the oxidizing converter.

The conditions of oxygen-rich oxidization taking place in the converter may vary in some respects depending on the constituents injected therein. For example, solvents used in the liquid chromatograph may be flamable solvents, such as acetone, or inflammable solvents, such as water. It will be understood that an appropriate solvent may be selected to dissolve the sample so that none of the elements which are to be detected are present in the solvent. As a result, trace compounds may be detected without being masked by the solvent and without requiring removal of the solvent prior to detection. Oxidation occurs approximately in the range 600° to 1800° C. Between 1750° C and 1850° C elemental nitrogen begins to oxidize to produce NO. Above approximately these temperatures such production of NO tends to constitute interference which deteriorates sensitivity of the instrument. Below 600° C conversion of combined nitrogen will be oxidized, the exact operating temperature being variable depending on sensitivity and selectivity desired. A preferred temperature range for most applications is 900° C to 1150° C. The solvent, oxygen and sample are thoroughly mixed to produce conversion to nitrogen oxide of the bound nitrogen in organic nitrogen containing compounds. Mixing, and thus oxidation, can be facilitated by packing at least a portion of the converter with inert particles, such as ceramic particles. An inert particulate packing within at least a portion of the furnace is particularly useful to enhance complete oxidation when inflammable solvents are used.

External heaters may be used to maintain the temperature of the furnace at a preset level in the range mentioned above. If flammable solvents are used, the solvent-sample-oxygen mixture may burst into flame in the coverter, in which case external heaters are used to a lesser extent or not at all, as required to maintain the desired temperature. If the solvent is highly flammable, it may tend to combust at or very near the nozzle tip. This can produce overheating of the converter, and of the nozzle in some cases. To avoid this, it may be desirable to introduce an inert gas with the oxygen to slow the reaction and produce oxidation further downstream in the converter.

When the organic compounds within the sample contain nitrogen and the system is operated to detect such nitrogen-containing compounds, effluent from the converter is directed to a nitric oxide analyzer. The reaction taking place in the converter converts the nitrogen to nitric oxide according to the following general reaction:

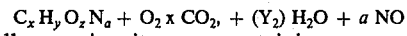

All organic nitrogen containing compounds which are fully oxidized will combine, as indicated above, to produce carbon dioxide, water and nitric oxide. Accordingly, the reading from the nitric oxide detector provides a measure of nitrogen containing organic compounds in the original sample. When necessary, a cold trap or other type of trap may be introduced between the converter and the gas detector for removing an excess volume of water or other interfering materials. If it is desirable to remove solvents prior to their detection, the cold trap is an effective means by which this can be accomplished. One circumstance which could dictate the necessity of a cold trap might be that where, for some reason, it is desirable to use a solvent which tends to mask the element which is to be detected by the gas detection device. It should be understood, however, that water, carbon dioxide and most other contaminants do not influence the reading if a highly selective nitric oxide detector, such as a chemiluminescent analyzer, is used.

When the sample subjected to liquid chromatographic analysis includes sulphur-containing compounds and it is desired to detect such compounds, the system operates in a similar fashion to that described above in connection with nitrogen compounds, a sulphur dioxide analyzer being substituted for a nitric oxide analyzer. The reaction taking place in the converter is according to the following general formula:

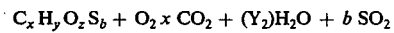

As can be seen from the above general reaction, sulphur in the organic sulphur containing compound is converted to $SO_2$ whereas carbon and hydrogen are oxidized to carbon dioxide and water, respectively. The gas instrument selective to sulphur dioxide will provide a reading functionally related to the sulphur-containing organic compounds in the sample. One suitable sulphur dioxide instrument is the Model 43 fluorescent $SO_2$ detector manufactured and sold by Thermo Electron Corporation of Waltham, Mass., U.S.A. or as described in U.S. Pat. No. 3,845,309. Other examples of compatible $SO_2$ analyzers are detectors based on a flame photometric principle, an ultraviolet absorption principle or a coulometric principle.

The ultimate sensitivity of the analyzing system of this invention is dependent, among other things, on the sensitivity of the ultimate gas analyzer. Chemiluminescent analyzers for detecting nitric oxide in a mixed gas sample are sensitive in the range of 1 part in $10^9$. Analyzers sensitive to sulphur dioxide such as the Model 43 fluorescent analyzer mentioned above, are sensitive in the range of 1 part in $10^6$. These instruments can be compatibly coupled to the output from the high pressure liquid chromatographic device through the converter described above. Important to the operation of the converter is its facility to mix the constituents from the liquid chromatograph with the oxygen and, in turn, the means for introducing liquid chromatograph effluent into the converter is one on which optimized performance depends.

The atomizing nozzle for admitting effluents from the liquid chromatograph to the converter is one which optimizes performance, particularly for samples including non-volatile constituents to be measured. While volatile constituents tend to oxidize more readily, it is particularly difficult to produce total molecular contact between the non-volatile constituents and oxygen to assure that complete oxidation of the constituents in the sample to be measured occurs. Suitable nozzle configurations may vary. For example, fluid mixing nozzles, preferred examples of which will be described below, and ultrasonic atomization nozzles may be used. Excellent results have been obtained with liquid nozzles which introduce materials into the converter along paths which are concentric one with the other. In the preferred embodiment, effluent from the liquid chromatograph is introduced into the converter in the form of a thin jet, through an elongated tube. Surrounding this tube is a second tube through which oxygen or other gases are admitted. The gases then form an output surrounding, or approximately surrounding, the jet of chromatograph effluent to break it up and disperse it into small particles, thereby atomizing it. A dual tube arrangement of the type referred to in the previous sentence may be used, or, if more numerous inputs to the furnace are desired, additional concentric tubes may be used to establish additional concentrically arranged flow paths.

DETAILED DESCRIPTION OF THE DRAWINGS

Figure 1:
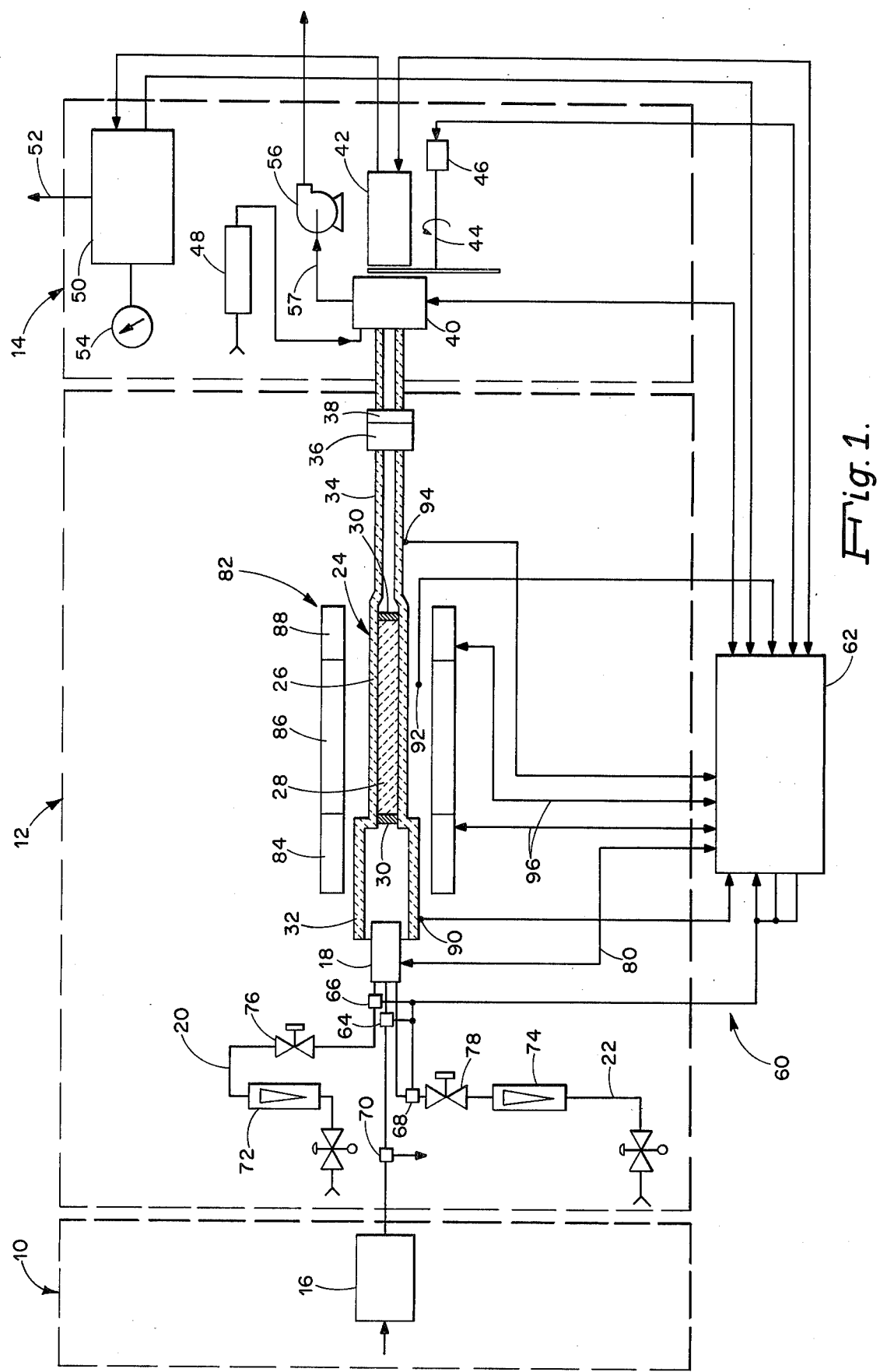
FIG. 1 is a schematic diagram illustrating a preferred embodiment of the invention.

FIG. 1 illustrates a preferred embodiment of this invention including three fundamental components, a liquid chromatograph 10, an oxidizing converter 12 and a nitric oxide detector 14. The liquid chromatograph 10 separates constituents in a liquid mixture and provides an effluent with the constituents being in timewise separation. Effluent is injected into the converter and oxidized. The oxidation products from the converter are then introduced to the nitric oxide detector 14. The nitric oxide detected by the detector 14 provides a reading of the nitrogen containing organic compound included in effluent from the chromatograph 10. The apparatus and its method of operation is more fully described below.

The chromatograph 10 includes a chromatographic column 16 used in association with a high pressure pump, not shown in FIG. 1, for forcing liquids through the column 16. The sample suspected of including nitrogen-containing organic compounds is presented in a liquid form, possibly dissolved in a solvent, to the liquid chromatograph 10. As the sample is forced by the high pressure pump through the chromatographic column 16, various constituents in the sample are separated from each other and discharged from the column 16 individually in timewise distribution. Each constituent can be identified by its time of discharge from the column. It is important in passing effluent from the chromatographic column through the converter 12 and the nitric oxide detector 14 that the timewise distribution of the constituents be maintained. In this manner output of the analyzer 14 is properly associated with the appropriate constituent.

To maintain the timewise distribution, the effluent from the chromatograph is introduced to a nozzle means 18, to be described in detail subsequently. The nozzle means 18 also receives oxygen from the oxygen supply means 20 and, optionally, may receive an inert gas through the inert gas supply means 22. The nozzle means 18 atomizes effluent from the column 12 and introduces it into an oxidizing chamber means 24. The chamber means is associated with an electrical heating means 82 for maintaining the chamber temperature at a selected level.

The oxidizing chamber means 24 is of a construction which will intimately mix the effluent from the chromatographic column and the oxygen so that all combined nitrogen in organic compounds of the sample are oxidized. Oxidation may be with or without combustion. The chamber means described below is one which provides successful operation for all types of chromatograph column effluents and solvents, including volatile and non-volatile effluent sample constituents and including flammable and inflammable solvents. Fundamentally, the chamber means 24 comprises an elongated tubular section 26 in which the reaction takes place. To promote mixing of the reactants, the member 26 may be filled with an inert particulate material 28, such as ceramic balls, which mix oxygen and chromatograph effluent. The inert particulate packing material 28 is particularly desirable for reactants which include either a non-volatile constituent or an inflammable solvent. The particulate material is held in place by perforated or porous members 30. The oxidizing chamber means 24 may also include an enlarged foresection 32 which receives the discharge from the nozzle means 18. This chamber provides preliminary mixing of the materials before they enter the packed bed of inert particulate material 28. Also, this enlarged forechamber may serve as a combustion chamber where highly flammable constituents experience at least the initial phases of combustion prior to entering the particulate bed 28. In situations where the forechamber 32 might tend to overheat, inert gas supplied through the inert gas supply means 22 may serve to slow the reaction and maintain an acceptable temperature range within the forechamber 32. Downstream from the tubular member 26 there may be an aft chamber 34 of reduced diameter. The chamber may be necessary to physically conduct the combustion products from the chamber means 24 to the gas analyzer 14. The aft chamber 34 is of reduced diameter to increase flow rate and reduce the time required for materials to travel its length. It is desirable to minimize transit time through the aft chamber to avoid a loss therein of nitric oxide, which tends to oxidize under certain conditions. The nitric oxide passing through the aft chamber is in the presence of the remaining oxygen introduced into the chamber means 24. The nitric oxide tends to oxidize to nitrogen dioxide, the reaction being temperature and time dependent. At higher temperatures, the nitric oxide tends to be stable and, as temperature is lowered, nitrogen dioxide tends to be produced. For further information relating to the stability of nitric oxide see "Principle of Operation of the Thermal Energy Analyzer of for the Trace Analyzing Volatile and Non-volatile N-Nitroso Compounds" by D. H. Fine, D. Lieb and F. Rufeh; *Journal of Chromatography,* 107 (1975) 351 – 357.

The oxidizing converter 12 may also include a trap 36 which may be a cold trap to remove unwanted constituents from the gas stream. Additionally, a throttling means 38 may be used to produce a pressure drop if reaction in the nitric oxide detector 14 is to be carried out at sub-atmospheric pressure.

From the aft chamber 34 the oxidized effluent from the oxidizing reaction chamber means 24 enters the gas detector 14. The gas detector 14 may be any suitable instrument for measuring oxidized nitrogen. For example, the detector may measure NO directly or convert NO to $NO_2$ and measure $NO_2$. An instrument of the chemiluminescent type is illustrated schematically. A chemiluminescent reaction chamber 40 is associated with a photomultiplier tube assembly 42. A shutter 44 driven by a motor 46 may be interposed between the photo-multiplier tube and the reaction chamber to increase sensitivity. By use of the shutter, the tube assembly 42 alternately samples desired signal and a reference signal, such as to achieve a better signal to noise ratio. The chemiluminescent reaction chamber 40 is associated with an ozone ($O_3$) supply means 48. Reaction in the chamber 40 between the ozone and nitric oxide in the discharge from the chamber means 24 produces a chemiluminescent reaction in which electrically excited nitrogen dioxide is formed. The nitrogen dioxide decays back to its ground state with the emission of light which is detected by the photo-multiplier tube assembly 42. The intensity of light emitted in the chemiluminescent reaction is directly related to the number of moles of nitrogen in the sample discharged through the nozzle means 18. The chemiluminescent reaction occurs according to the following reaction:

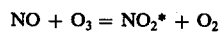

$$NO + O_3 = NO_2^* + O_2$$

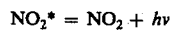

$$NO_2^* = NO_2 + h\nu$$

The photo-multiplier tube is associated with an appropriate signal processer 50 which can provide an output 52 for a recorder and a visual output indicator 54. If it is desired to operate the reaction chamber below atmospheric pressure, an appropriate vacuum pump 56 communicates with the chemiluminescent reaction chamber 40 through its exhaust means 57. During operation the vacuum pump 56 and the flow throttling device 38 cooperate to reduce the pressure in the reaction chamber 40 to a sub-atmospheric level. If operation is to be at atmospheric pressure, both the pump and the flow throttling device 38 are unnecessary. Typical chemiluminescent analyzers are disclosed in U.S. Pat. Nos. 3,746,513 and 3,763,877.

The system described above for detecting organic nitrogen containing compounds can be controlled by any suitable control system. The system can be relatively sophisticated or relatively simple. A control system 60 is illustrated schematically to identify various functional parimeters which can be detected or controlled in an operating system. A central electrical control 62 may detect operating conditions in various parts of the system and, in response thereto, determine operating conditions in various other parts of the system. For example, in response to detected conditions flow, temperature and pressure may be regulated as desired. The control system 62 will be described from the output of the chromatograph 16 through the detector 14. Chromatograph effluent is fed to the atomizing nozzle 18 of the oxidizing converter 12. As mentioned above, one function of the atomizing nozzle 18 is to enhance mixing of nitrogen-containing organic compounds from the chromatograph with sufficient oxygen from the oxygen supply means 20 so that oxidation of the nitrogen in the organic nitrogen-containing compound will be complete. In the preferred embodiment, oxygen is provided so that a combination of oxygen supply in excess of any anticipated stoichiometric mixture and very thorough mixing produces oxidation which is for all practical purposes complete.

Operation can be enhanced by automatic control of the feed of materials to the nozzle 18. For example, the electric control 62, as indicated by elements 64, 66 and 68, control the mixture of chromatograph effluent, oxygen and inert gas by establishing predetermined flow rates for each such constituent. On the other hand, element 64 may be a sensing device which determines the flow of chromatograph effluent to the nozzle means 18 and provides a signal, in response to which the control 62 operates elements 68 and 66 to control the flow of oxygen and inert gas to the nozzle. Element 70 may be used in conjunction with element 64 to bleed off a fractional portion of chromatograph effluent if the supply is larger in volume than that which is desirable to pass through the oxidizing converter 12 or the nitric oxide analyzer 14. It will of course be understood that flow control could be manual as by observation of flow indicating devices 72 and 74 and manual operation of valve means 76 and valve means 78.

As will be explained subsequently, the valve means 18 may include, as an optional feature, an internal heating unit. If included, this unit can be supplied with power from the electrical control 62, through means 80.

The heating means 82 may provide a single heating zone for maintaining uniform temperature or it may be provided with multiple zones 84, 86 and 88 for maintaining multiple temperature zones within the oxidizing reaction chamber means 24. In either event, the temperature established by the heating means 82 can be determined by the electrical control 62. Temperature sensors located at various points within the oxidizing chamber means 24 determine operating temperature. If the heating means 82 is constructed to provide a single heating zone and if it surrounds at least a portion of the oxidizing reaction chamber means 24, as shown in FIG. 1, the portion of the oxidizing reaction chamber means 24 surrounded by the heating means 82 will tend to be at a uniform temperature except for such cooling as may occur as a result of relatively cool flow entering the chamber means 24 through the nozzle means 18. On the other hand, if independent heating zones 84, 86 and 88 are established, clearly differential temperatures can be established in the forechamber 32, the tubular member 26 and the aft chamber 34. For example, thermocouples 90, 92 and 94 can be provided for sensing the temperature, respectively, in the enlarged forechamber 32, the tubular member 26 and the aft chamber 34. Signals from the thermocouples are transmitted to the electrical control 62 which variably governs power supply to the heating means 82 in response thereto, the power supply being furnished through means 96.

Figure 2:
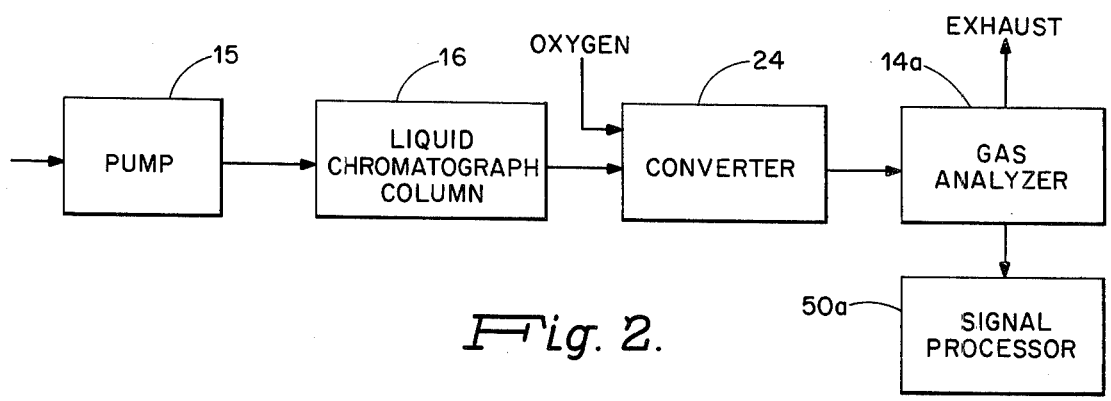
FIG. 2 is a block diagram illustrating the present invention.

FIG. 2 is a block diagram illustrating the invention generally and consistent with the embodiment described in FIG. 1. Like numerals are used to designate like parts. A pump 15 supplies the driving pressure for the liquid chromatograph column 16. Flow rates in the range 0.1 to 0.8 ml/min are used in the preferred embodiment. Effluent from the column 16 is fed to the oxidizing converter 24, as described above in connection with FIG. 1. The oxidizing reaction taking place in the converter is such that, in addition to nitrogen-containing organic compounds, sulphur-containing organic compounds react. On the one hand the sulphur and on the other hand the nitrogen is oxidized. In compounds containing both sulphur and nitrogen, both oxidation reactions occur substantially simultaneously. When it is desired to measure the content of organic sulphur-containing compounds in a sample, the gas analyzer 14A is a suitable sulphur dioxide analyzer associated with an appropriate signal processor 58. Otherwise, the method and apparatus of the present invention is substantially the same for both sulphur-containing and nitrogen-containing organic compounds.

Figure 3:
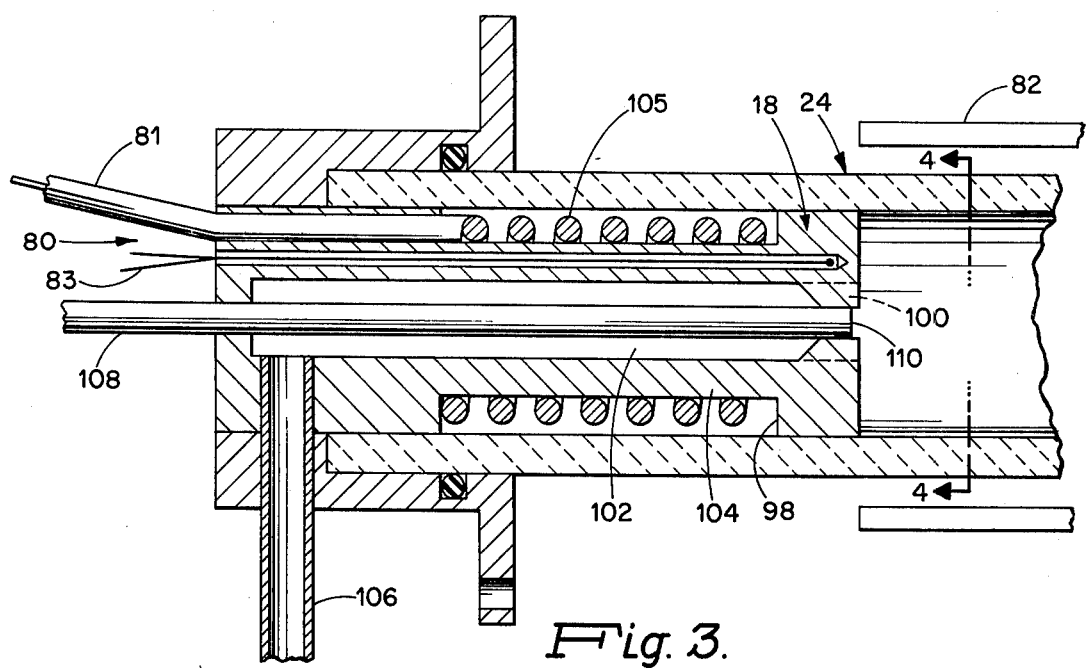
FIG. 3 is a sectional view showing a portion of the apparatus illustrated in FIG. 1.

FIG. 3 is a detailed cross-sectional view showing the nozzle means 18. The nozzle means 18 extends into the upstream end of the chamber means 24 and is provided with an outwardly extending collar 98 which abuts the inner surface of the chamber means 26. The nozzle means 18 is provided at its terminal end with a means 100 forming an opening or ports for ejection of oxygen into the reaction chamber formed by the chamber means 24. The opening means 100 communicates with a tubular chamber 102 formed by the body 104 of the valve means 18. An inlet 106 communicates with the oxygen supply means 20 and, if used, the inert gas supply means 22. Extending through the tubular chamber 102, concentrically therewith, is an effluent feed means 108 from liquid chromatograph 16. Effluent from the chromatograph is fed through the means 108 to a discharge port 110 in its terminal end and discharged into the reaction chamber.

Surrounding the body 104 of the valve means 18 is the electrical heating means 80 comprising the thermocouple 83 and a resistance heater 105. The thermocouple senses the temperature of the valve means 18 adjacent the port means 100 and port 110 and provides a signal to the electrical control system 62. The electrical control system, in response to the signal, provides energization to the resistance heater 105 for maintaining the nozzle means 18 at a predetermined temperature. Thusly, the nozzle 18 may preheat its inputs from the feed means 108 and the inlets 106 prior to their ejection from the nozzle into the reaction chamber. Alternately, if independent temperature control is not required, the heating means 82 may extend to the proximity of the discharge end of the nozzle means 18, as shown in FIG. 3, so that heat therefrom will maintain the discharge end at a temperature predetermined by reaction chamber temperature. Also, both heating techniques may be used in conjunction.

Figure 4:
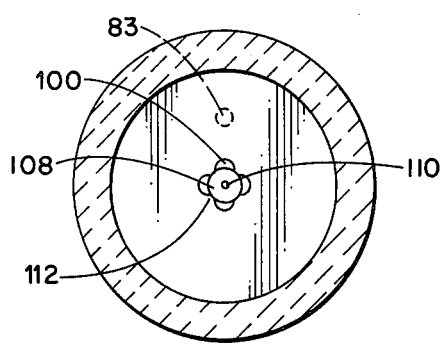
FIG. 4 is a view taken along line 4—4 of FIG. 3.

Ports 100 and 110 may be of various configurations. It is essential however that they be constructed to atomize the effluent from the liquid chromatograph. Atomization is beneficial in all applications and it is of particular benefit when non-volatile effluent constituents from the liquid chromatograph are to be oxidized, for the reasons described above. One embodiment, illustrated in FIG. 4, shows the effluent feed means 108 and its associated port 110 arranged centrally within the port means 100. The port means 100 comprises four separate outlets arranged at equal angular intervals about the port 110. Between each of the individual outlets is a portion 112 which extends inward, into contact with the outer surface of the feed means 108. This construction serves to securely position the feed means and to restrict the outlet for oxygen.

Figure 5:
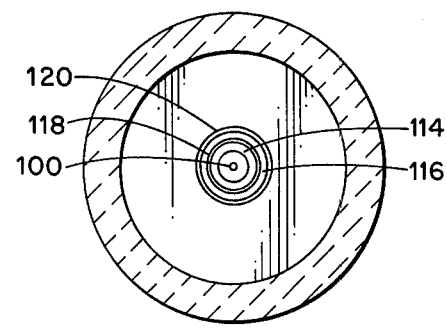
FIG. 5 is a view similar to FIG. 4 illustrating an alternate embodiment of the invention.

FIG. 5 illustrates an alternate embodiment of the nozzle means 18 where three constituents are fed individually into the reaction chamber formed by the chamber means 24 through concentrically arranged feed means. The central feed forms the port 100 through which effluent from the liquid chromatograph is fed. Other constituents are fed through concentrically arranged ports 114 and 116 formed by tubular members 118 and 120, respectively. In this embodiment, the oxygen can be fed through the port 114 and an inert gas may be maintained separate from it and fed through the port 116. One advantage of the construction of FIG. 5 is that, under circumstances when the reaction chamber in the chamber means 24 tends to overheat in the vicinity of the nozzle means 18, the inert gas fed through the outermost concentric feed passage 116 slows the oxidizing reaction and has a cooling effect on the walls of the chamber means 24 in the region adjacent the nozzle means 18. It will be appreciated that additional concentric tubes may be provided for individually supplying other constituents to the reaction chamber as desired.

Several examples of systems operating in accordance with the present invention will be described.

EXAMPLE 1

Figure 6:
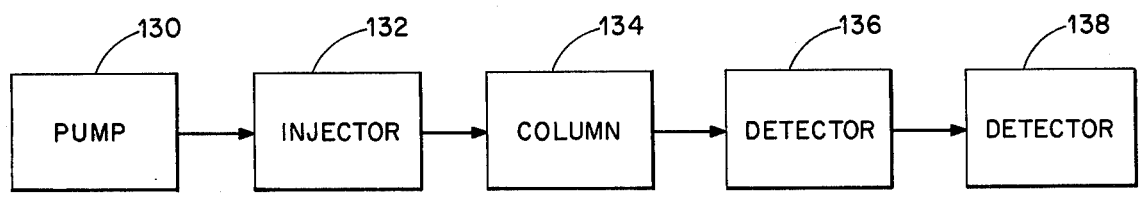
FIG. 6 is a block diagram illustrating a specific embodiment of the invention.

This example will be described in connection with FIGS. 6 and 7. A Waters Associates (Milford, Mass., U.S.A.) Model 6000A high pressure liquid chromatograph pump 130 was connected in series to a Waters Associates Model U6K Injector 132, a Waters Associates u-Bondapak-$NH_2$ liquid chromatographic column 134, a Waters Associates Model 440 ultra-violet absorbance detector 136 monitoring absorbance at 254 nm and a Thermo Electron Model 512 nitrogen specific detector 138 operating with an oxidizing reaction chamber temperature of 1085° C. (The Model 512 detector consists of the oxidizing converter 12 and the detector 14 shown in FIG. 1.) The ultraviolet absorbance detector 136 does not demonstrate the selectivity or sensitivity of the nitrogen specific detector 138 and is not an essential part of the system of this invention. However, it was used in the examples herein described so its results could be compared to the results ultimately achieved from the nitrogen specific detector 138. The ultraviolet detector 136 operates in the liquid phase and is non-destructive of its sample input. Its output is delivered to the nitrogen specific detector 138 in the same condition as if effluent had been fed directly from the chromatographic column 134 to the detector 138.

The separation of hydantoin, ethylene urea and ethylene thiourea was achieved using hexane: methanol: 2-propanol (10:2:1) as a carrier solvent at a flow of 0.5 milliliters per minute. The injector and the pump are used, respectively, to introduce the sample into the column and to deliver carrier solvent isocratically.

Figure 7:
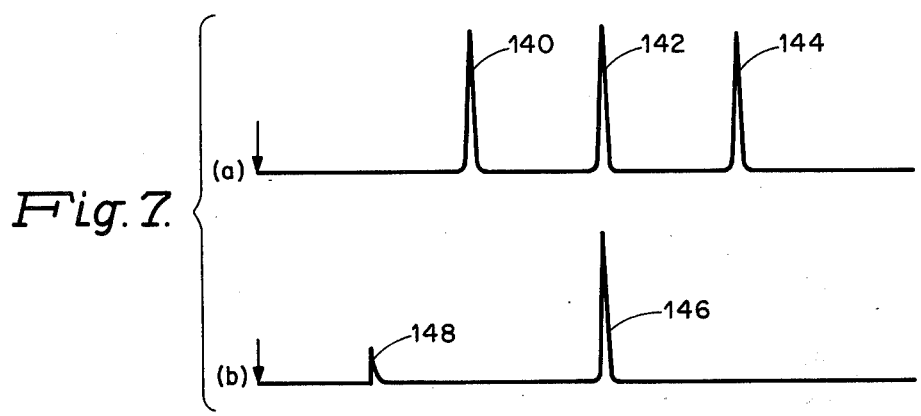
FIGS. 7 and 8 show chromatograms resulting from apparatus of the type illustrated in FIG. 6.

In FIG. 7, the separation of ethylene urea and ethylene thiourea and hydantoin is illustrated, the three being represented, respectively, by peaks 140, 142 and 144 in the chromatogram of FIG. 7A. Because of low molar absorbtivity at 254 nm, ethylene urea and hydantoin are not detected by the ultraviolet absorbent detector but ethylene thiourea is detected and represented by peak 146 in the chromatogram of FIG. 7B. Peak 148 is a solvent front.

EXAMPLE 2

This example will also be described in connection with FIG. 6. The chromatogram associated therewith is shown in FIG. 8.

A Spectra Physics (Santa Clara, Calif., U.S.A. 95051) Model 740B pump 130 was connected in series to a Waters Associates Model U6K injector 132, a Waters Associates u-$C_{18}$ Bondapak Liquid chromatographic column 134, a Waters Associates Model 440 ultraviolet absorbance detector 136 monitoring absorbants at 254nm and a Thermo Electron Model 512 nitrogen specific detector 138 operating with an oxidizing reaction chamber temperature of 1070° C.

A measure of caffein present in a sample was achieved using 6.7% 2-propanol in 1% acetic acid in water as a carrier solvent, with a flow rate of 0.5 ml per minute. The sample injector and solvent pump provide the constituents to the chromatographic column 134 and thereafter to the detectors 136 and 138.

Figure 8:
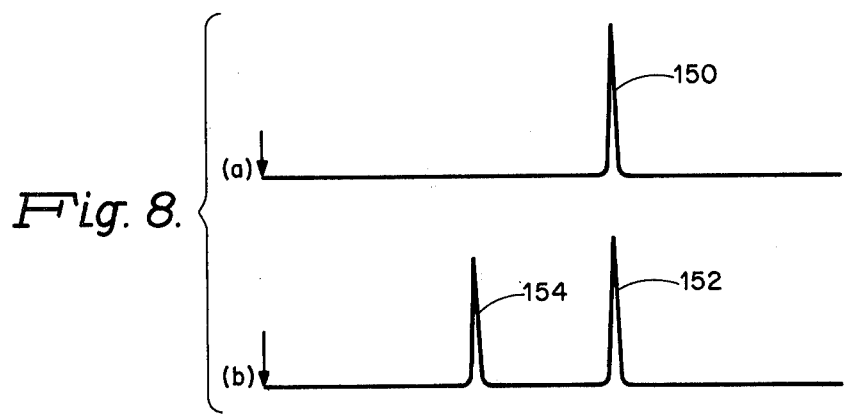

In FIG. 8, the separation of caffein from the sample is illustrated. In FIG. 8(a), the chromatogram resulting from the nitrogen specific detector 138 is illustrated, the peak 150 representing cafein. In FIG. 8(b), caffein is detected and represented by peak 152 in the chromatogram of the ultraviolet abosrbant detector 136. Peak 154 shown in FIG. 8(b) represents the solvent front.

COMMENTS ON EXAMPLES

The system of the above examples is uniquely selective to nitrogen containing organics, there being no known interference. The response is molar, being proportional to the number of nitrogen atoms present in the molecule. The sensitivity of the system of the examples appeared limited by the background level of the nitrogen containing organic compounds present in the best "distilled in glass" high pressure liquid chromatograph solvents being used. Solvents apparently tend to contain a background impurity level involving nitrogen containing organics but in the best "distilled in glass" solvents these appear minimal. Obviously, solvents should be selected which do not otherwise contain organic nitrogen containing compounds. Approximately 100 pg ($10^{-10}$ g) of nitrogen containing compounds are required for detection in the apparatus of the above-described example.

Additionally, solvents which contain halogens were converted to their corresponding acid halides and need specific handling to avoid deterioration of the equipment. Otherwise, such solvents do not appear to effect the accuracy of the system. Also, it was found that solvents containing inorganic buffers tended to produce precipitates in the nozzle.

In the above examples, the tubular member 26 is of an inert ceramic material such as alumina, although other materials such as glass or quartz could be used. The tubular member is 9 inches long, ⅜ inch in diameter and packed with approximately spherical inert ceramic particles 0.030 to 0.060 inches in diameter. The forechamber 32 is open and also 9 inches long and ⅜ inch in diameter. Of the overall 18 inch length, the central 12 inches is surrounded by a heating means. Generally, the tubular member may be short (to approximately 5 cm.) or long (to approximately 50 cm.) and may range in diameter from 0.5 cm. to 2 cm. The range for the diameter of the forechamber is approximately the same as that for the tubular member, although the tubular member will frequently be in the lower part of the range while forechamber will frequently be in the upper part of the range. The length of the forechamber will typically be between 10 cm. and 25 cm.

The invention may be embodied in other forms without departing from its essential characteristics. The present embodiments are therefore to be considered illustrative and not restrictive, the scope of the invention being indicated by the appended claims rather than the foregoing description.

I claim:
1. A chromatograph analysis system comprising:
   a. a liquid chromatograph for separating constituents of a liquid sample and discharging the separated constituents in timewise distribution;
   b. converter means for reacting liquid effluent from said chromatograph with a gaseous reactant approximately in the temperature range 600° to 1800° C;
   c. atomizing nozzle means comprising:
      i. liquid discharge means extending from said chromatograph into said converter means for discharging into said converter means constituents separated in said chromatograph such discharge into the converter means being in the timewise distribution established in said chromatograph; and
      ii. gaseous reactant discharge means extending into said converter means and surrounding said liquid discharge means for discharging the gaseous reactant into said converter means in a pattern surrounding said liquid discharge means; and
   d. specific gas detector means for receiving discharge from said converter means.

2. The system of claim 1 further comprising means for heating said nozzle means.

3. The system of claim 2 wherein said heating means comprises an electrical heating element within said converter means adjacent said nozzle means.

4. The system of claim 2 wherein said heating means comprises said converter means and a heating element external of said converter means.

5. The system of claim 1 wherein at least a portion of said converter means is packed with inert particulate material.

6. The system of claim 5 wherein said converter means is elongated and comprises an unpacked portion between said packed portion and said nozzle means.

7. The system of claim 6 wherein said unpacked portion defines a cross-sectional area normal to the longitudinal axis of said converter means which is larger than such cross-sectional area of said packed portion.

8. The system of claim 6 wherein said converter means comprises an elongated conduit of inert ceramic material.

9. The system of claim 8 further comprising a portion of said converter means between said packed portion and said specific gas detector having a cross-sectional area normal to the longitudinal axis of said converter means which is smaller than such cross-sectional area of said packed portion.

10. In a chromatographic analysis system including a liquid chromatograph and an elongated conduit forming a heated reaction chamber, a nozzle for introducing reactants into said conduit comprising:
   a. an elongated tube extending from said chromatographic into said conduit for discharging into said conduit for discharging said conduit constituents separated in said chromatograph, such discharge into the conduit being in the timewise distribution established in said chromatograph;
   b. gaseous reactant discharge means extending into said conduit and surrounding said tube for discharging gaseous reactant into said conduit in a pattern surrounding said tube;
   c. means for preventing escape of reactant from between said tube, said gaseous reactant discharge means and said conduit.

11. In the system of claim 10, heating means surrounding said gaseous discharge means.

12. In the system of claim 10, means interposed between said tube and said gaseous reactant discharge means forming a plurality of gaseous discharge openings surrounding said tube.

13. In the system of claim 10, a gaseous discharge means for a plurality of gases comprising concentric tubes surrounding the first said tube.

14. A method of chromatograph analysis of nitrogen containing organic compounds comprising the steps of:
   a. chromatographically separating constituents of a liquid sample and discharging the separated constituents in timewise distribution;
   b. reacting in a converter organic nitrogen compound containing liquid effluent from said chromatograph with oxygen approximately in the temperature range 600° to 1800° C to produce nitric oxide;
   c. discharging chromatographic effluent into the converter in the timewise distribution established in said chromatograph; and
   d. discharging oxygen in said converter in a plurality of streams surrounding the chromatographic effluent for atomizing the effluent; and
   e. detecting the nitric oxide produced.

* * * * *